United States Patent [19]
Freiberg et al.

[11] Patent Number: 5,422,899
[45] Date of Patent: Jun. 6, 1995

[54] HIGH REPETITION RATE MID-INFRARED LASER

[75] Inventors: Robert J. Freiberg, Thousand Oaks; Colette Cozean, El Toro, both of Calif.

[73] Assignee: Premier Laser Systems, Inc., Irvine, Calif.

[21] Appl. No.: 240,255

[22] Filed: May 10, 1994

[51] Int. Cl.⁶ .............................................. H01S 3/10
[52] U.S. Cl. .......................................... 372/25; 372/35
[58] Field of Search ................................... 372/25, 35

[56] References Cited
U.S. PATENT DOCUMENTS

4,713,820 12/1987 Morris et al. .
4,881,233 11/1989 von Arb et al. .

Primary Examiner—Léon Scott, Jr.
Attorney, Agent, or Firm—Knobbe, Martens, Olson & Bear

[57] ABSTRACT

An optically pumped mid-infrared solid-state laser with high pulse repetition rate is described for use in laser surgery. The laser produces a wavelength between 1.7 and 4.0 microns, and is optically pumped. The rise and fall times of the pump pulses are sufficiently short to avoid thermal lensing induced instability. The laser provides an increased rate of tissue cutting without necessitating an increase in the pulse energy.

14 Claims, 6 Drawing Sheets

HIGH REPETITION RATE MID-INFRARED LASER

FIELD OF THE INVENTION

The present invention pertains generally to pulsed lasers for surgical applications, and in particular to optically pumped infrared solid-state lasers with high pulse repetition rate.

BACKGROUND OF THE INVENTION

Current medical practice often relies upon laser energy for various surgical operations. Laser light is capable of cutting, ablating and cauterizing tissue as well as coagulating blood.

Yttrium Aluminum Garnet (YAG) is a host crystal whose dopant-derived lasers emit primarily in the infrared, and are widely used for a variety of surgical applications. Erbium-doped YAG (Er:YAG) laser emission, at a wavelength 2.94 $\mu$m, is strongly absorbed by water and thus particularly effective for cutting tissue. When used for tissue surgery, these lasers are typically operated in a pulsed mode, and their rate of cutting is commonly controlled by adjusting the optical energy of the pulses. Unfortunately, increasing the pulse energy to provide more aggressive cutting can result in microfracturing of hard tissue and excessive heating in healthy, outlying soft tissue. Additionally, the lasers themselves may experience instabilities caused by transient heating of the YAG crystal from high pump powers, possibly even decreasing their cutting efficiency.

Thus, there is a clear need in the surgical laser art for a laser which increases cutting efficacy without the detrimental effects associated with high pulse energies.

SUMMARY OF THE INVENTION

According to one aspect of the present invention a pulsed, optically pumped laser produces pulses at a high repetition rate. A resonant cavity having a laser material is positioned for pumping by a source of pump light. A circuit energizes the pump source to produce pulsed optical pump energy at a pulse repetition rate greater than 10 pulses per second. The pump pulses pump the laser material at a repetition rate of more than 10 pulses per second, and preferably greater than 20 pulses per second. The pumped laser material emits light having a wavelength between 1.7 $\mu$m and 4.0 $\mu$m. The pulsed, high repetition rate optical pump energy has a rise time and fall time sufficiently short to avoid thermal lensing induced instability of the laser pulses in the laser cavity when operating at the aforementioned repetition rate.

The laser system may for example use a solid-state medium for laser transitions in the mid-infrared, such as Er:YAG operating above 10 pulses per second, or Ho:YAG preferably operating from 20 to 50 pulses per second, positioned to produce laser oscillation within an optical cavity. The source of pump light may be a xenon flashlamp, which is positioned adjacent to the laser medium to optically excite laser transitions therein. The electric circuit, may be an LC-type pulse-forming network. Preferably the pump circuit entails the use of a simmer supply, whereby the laser medium is pumped during the interpulse period to the extent that the laser-related electronic transitions are held substantially at, but below, laser threshold during the interpulse time period. When the energy required to maintain the laser medium at laser threshold is applied continuously, thermal equilibrium is established at an operating condition where additional pump energy, in pulsed form, will couple more efficiently into laser light. A further advantage provided by the simmer supply is that the pump power required to maintain the laser medium at threshold is less than the pump power required to bring the laser medium from quiescent conditions to threshold, which means the power dissipation is more uniformly distributed over time. A further synergistic advantage to the simmer supply is that the pump pulse energy can be smaller for a given laser output, with a consequent increase in response of the electronic pulse-forming network. All of these factors cooperate to avoid thermal instability, thereby allowing higher pulse repetition rate.

The laser preferably utilizes a reflective ellipsoidal pump cavity, whereby light from the pump source is directed onto the axis of the laser medium. In contrast to common optically diffusive pump cavities, the ellipsoidal cavity produces a more uniform gain profile within the laser medium and allows lower energy pump pulses to achieve a given laser output. Since less energy may be dissipated per pulse, thermal instabilities are attenuated, thereby allowing higher repetition rate. An additional feature of the preferred embodiment is the use of a pump spectral filter, which eliminates a substantial portion of the pump power not associated with the laser medium pump wavelengths. By eliminating excess energy deposition within the medium, the laser operates at higher pulse repetition rate before the onset of thermal lensing instability.

In accordance with another aspect of the present invention, a pulsed laser comprises a source of pump light and an optical resonator cavity, which in turn comprises a laser medium and reflectors. The laser medium emits light between 1.7 $\mu$m and 4 $\mu$m in response to pumping by the source of pump light. One of the reflectors is partially transmitting so as to produce laser light output from the optical resonator and at least one of the resonator reflectors is curved so as to at least partially compensate thermal lensing effects in the laser medium. A fluidic flow system cools the laser medium. The fluidic system is configured to provide a flow of fluidic coolant which is substantially laminar through a portion of the optical resonator cavity containing the laser medium, in a direction parallel to a surface of the laser medium except at the boundary between the fluid and surface of the laser medium. An electrical circuit energizes the source of pump light with electrical pulses having a ratio of total energy to peak power less than 500 $\mu$s. The electrical circuit also supplies sufficient energy to the pump source between the pulses to produce enough interpulse pump energy to maintain the laser medium substantially at, but below, the laser threshold during the interpulse period.

In accordance with still another aspect of the present invention, a surgical method comprises supplying light pulses at a wavelength between 1.7 $\mu$m and 4 $\mu$m at a repetition rate greater than 10 pulses per second and preferably greater than 20 pulses per second. The light pulses, which are directed against the tissue to be modified, have a pulse energy less than 1 Joule/pulse and preferably a radiant exposure of less than 2.0 J/mm$^2$/pulse. The light pulses are directed against the tissue by preferably transmitting the light through an optical fiber waveguide. One preferred optical fiber for mid infrared wavelengths is disclosed in copending U.S. patent application Ser. No. 08/075,720, which is incorporated by reference herein. In the preferred embodiment, the pulses have a pulse duration less than 500 μs, and for a number of exemplary applications, a pulse energy of 10 mJ to 250 mJ is preferred.

BRIEF DESCRIPTION OF THE DRAWINGS

FIG. 6 is a schematic cross section of (a) diffusive and (b) ellipsoidal pump cavities taken along line 6 of FIG. 1.

DETAILED DESCRIPTION OF THE PREFERRED EMBODIMENT

Figure 1:
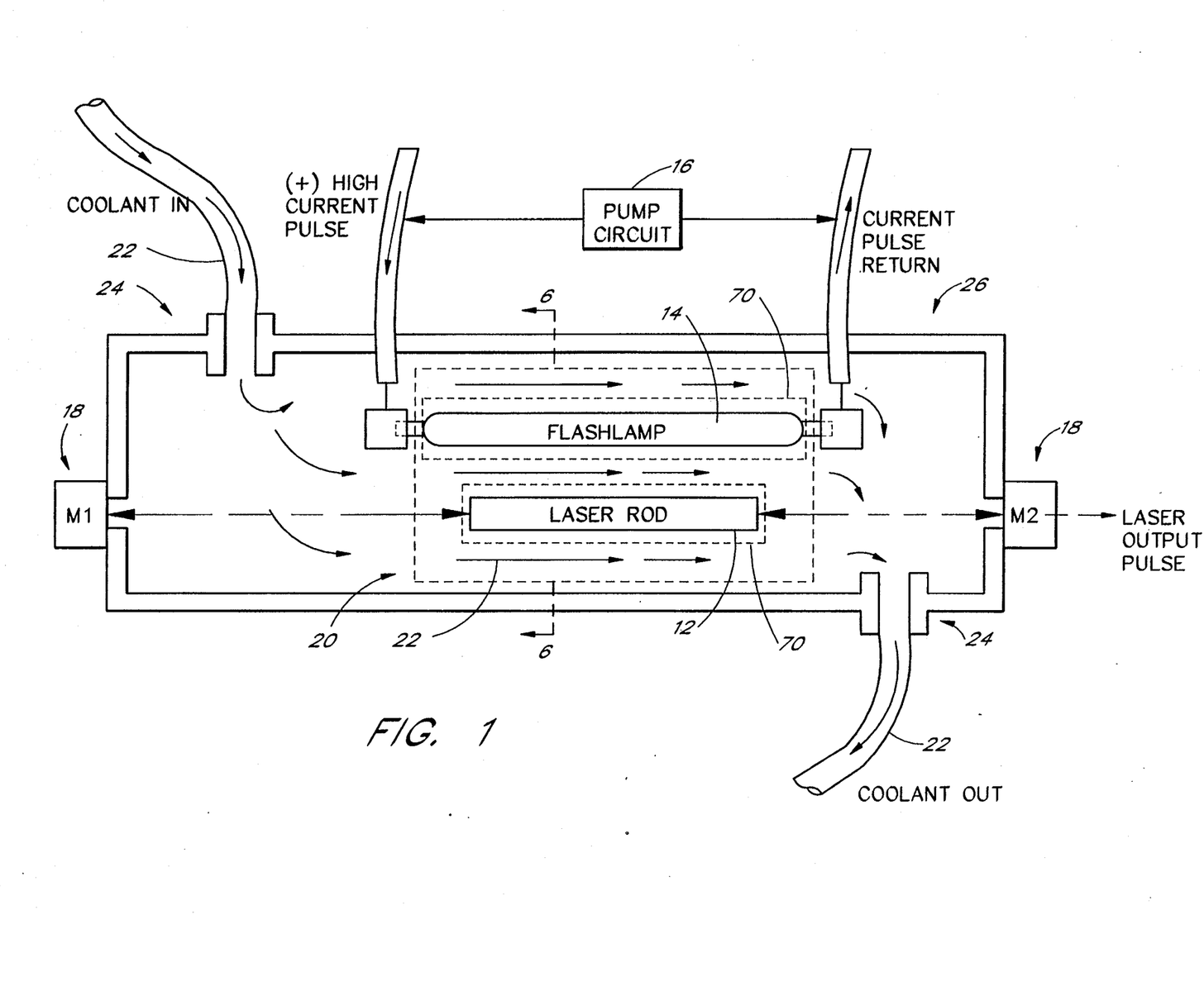
FIG. 1 is a schematic cross section of an optically pumped solid-state laser representative of the type discussed herein.

As shown in FIG. 1, an optically pumped solid-state laser 10, is comprised of a laser head 26, which houses an optical pump cavity 20 enclosing a solid-state laser medium 12 and an optical pump source 14. The laser medium 12, such as YAG crystal, is usually in the shape of a cylindrical rod positioned longitudinally with cylinder axis aligned within an optical resonant cavity defined by mirrors 18. The optical pump source 14, such as a gas discharge flashlamp, is positioned adjacent to the laser medium 12, both of which are enclosed by the optical pump cavity 20. The optical pump source 14 is electrically connected to a pump source drive circuit 16. Additionally, the laser head 26 is provided with inlet/outlet passages 24 for fluidic coolant 22 exchange and flow.

Figure 2:
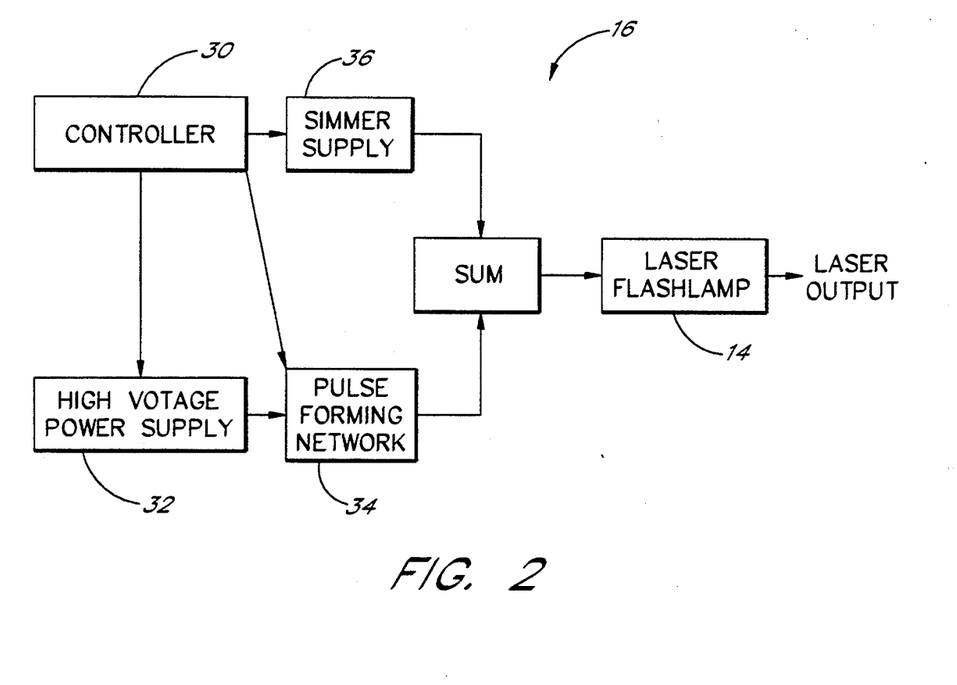
FIG. 2 is a functional block diagram of the pump light source drive circuit.
Figure 3:
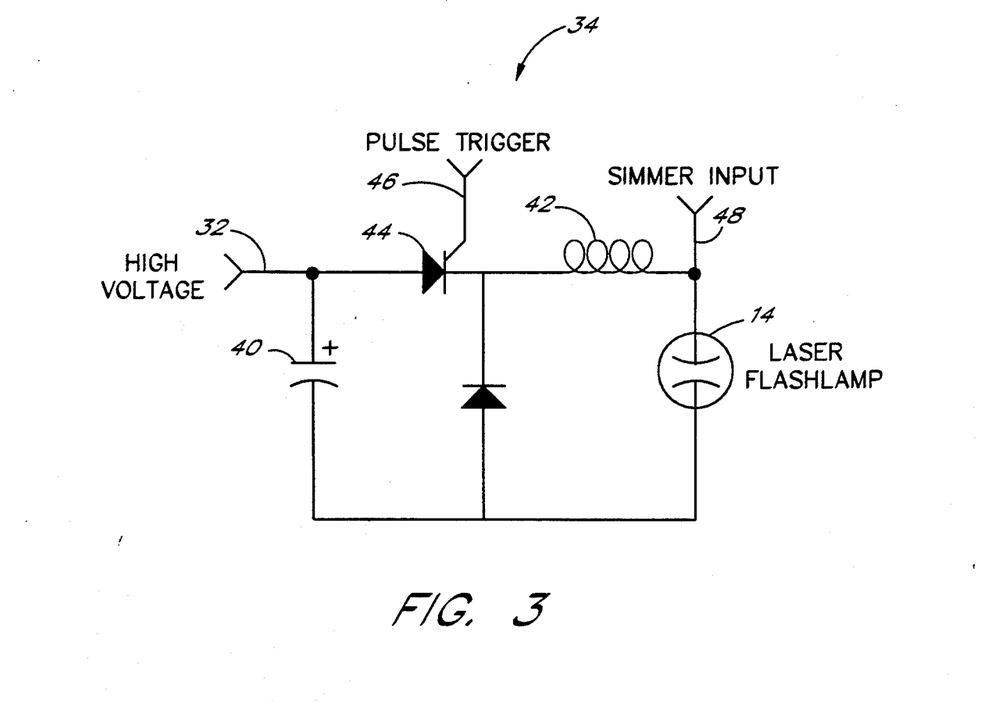
FIG. 3 is a basic schematic of the pulse-forming network appropriate to the preferred embodiment.

The optical pump source drive circuit 16 of the preferred embodiment, shown functionally in FIG. 2, comprises a controller 30, a high-voltage supply 32, a pulse-forming network 34 and a simmer supply 36. The controller 30 is connected to each of the high voltage supply 32, the pulse forming network 34 and the simmer supply 36. The high-voltage supply connects to the pulse-forming network 34 which in turn connects to the laser flashlamp 14, as does the simmer supply 14. The pulse-forming network 34 of the preferred embodiment, shown schematically in FIG. 3, is comprised of a series connected loop containing, in successive order, a storage capacitor 40, trigger switch 44, inductor 42 and flash lamp 14. There is a connection to the loop for the high voltage input 32, located between the storage capacitor 40 high voltage lead and trigger switch 44; another connection for the pulse trigger input 46 is located at trigger switch 44; and a connection for the simmer supply input 48 is located between inductor 42 and flashlamp 14.

Figure 6A:
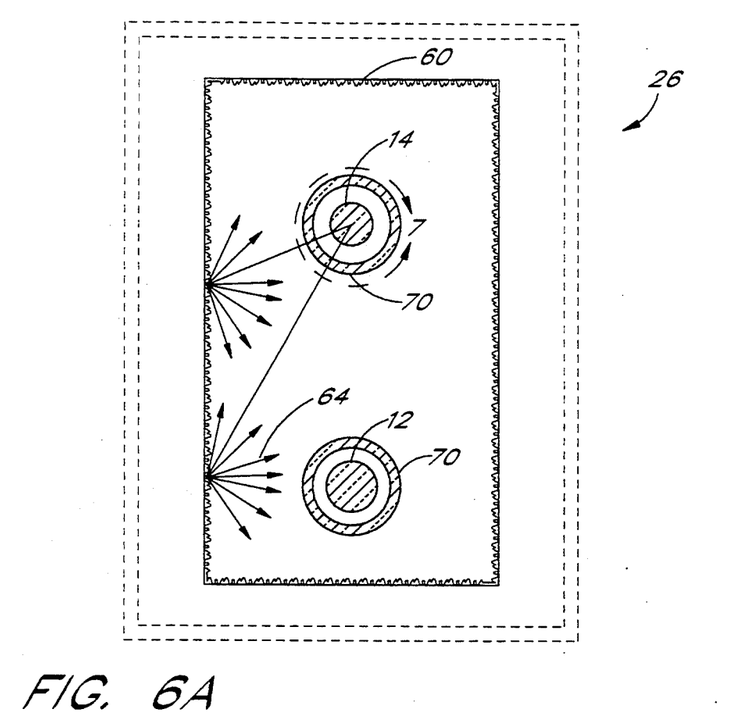
Figure 6B:
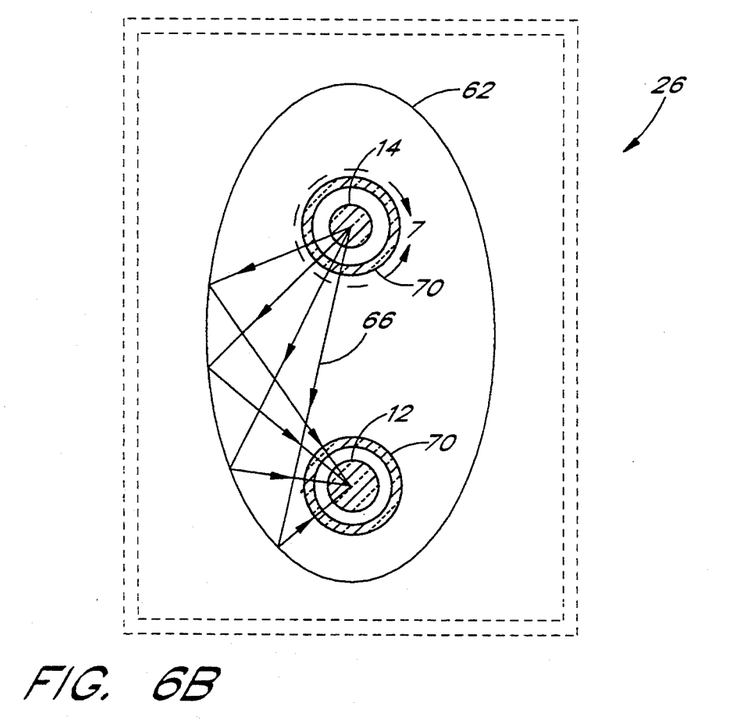

The optical pump cavity 20 encases both the flashlamp 14 and laser rod 12 as shown in cross-section by FIGS. 6a and 6b. FIG. 6a represents an optically diffusive cavity arrangement whose inner wall is rough on the scale of optical wavelengths, wherein flash lamp 14 and laser rod 12 are placed. FIG. 6b comprises a reflective cavity 62 of ellipsoidal cross-section, wherein the axis of flash lamp 14 and laser rod 12 coincide with the ellipse foci. Rays 64 and 66 represent the paths of light rays emitted by flashlamp 14 within cavities 60 and 62, respectively. Additionally, in the preferred embodiment, the flashlamp 14 is positioned concentrically within a cylindrically shaped spectral filter 70 as shown in perspective in FIG. 7a.

Figure 8:
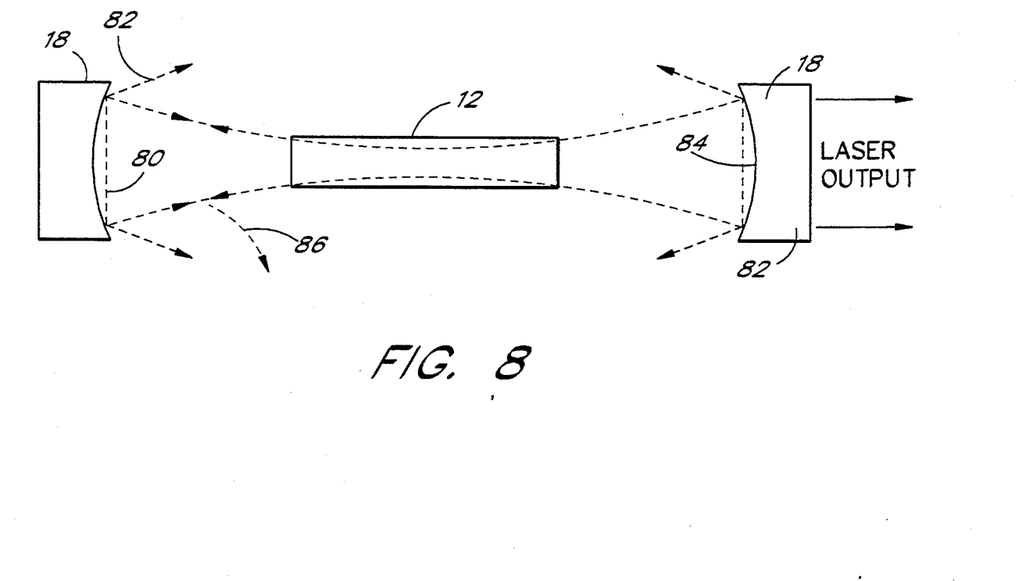
FIG. 8 is a cross-section of the laser optical cavity stabilized by corrective end mirrors.

The optical resonant cavity, shown cross-sectionally in FIG. 8, has an optical axis defined by mirrors 18, within which is positioned laser rod 12 such that the optical axis of laser rod 12 coincides with the optical axis of the resonant cavity. The mirrors 18 may have flat faces 80, but as discussed later, the preferred embodiment entails the use of curved mirror faces 84. Light rays, 82 and 86, represent laser oscillation within the optical resonant cavity for the case of flat and curved faces, respectively.

Figure 9:
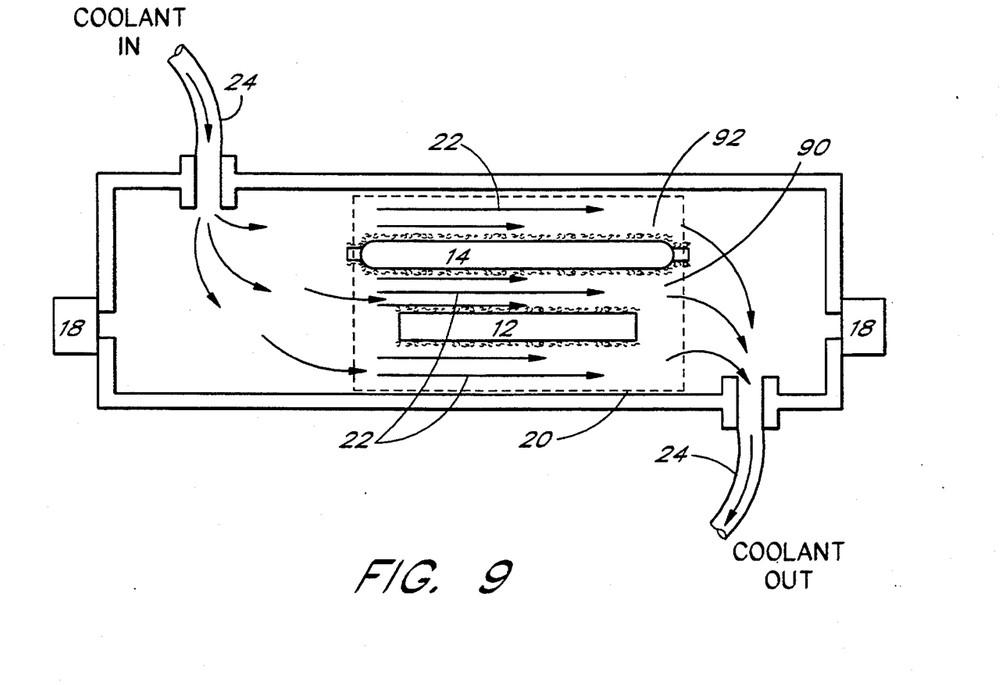
FIG. 9 is a schematic cross-section of a fluidic cooling system maintained in substantially laminar flow.

The laser head 26 is provided with a fluidic cooling system, which is comprised of fluidic coolant 22 and inlet/outlet ducts 24 for passage thereof. As shown in FIG. 9, the components within laser head 26, such as flashlamp 14, laser rod 12 and pump cavity 20, are arranged to be in intimate contact with flowing fluidic coolant 22, such that the predominant flow pattern is parallel to all heat-bearing surfaces. Fluidic flow regions 90 and 92 represent laminar and non-laminar flow, respectively.

The general operation of an optically pumped solid-state laser 10 begins with a condition of so-called negative temperature or population inversion between energetic levels of the laser medium 12. The solid-state laser medium 12 is usually comprised of a host material containing active ions which are optically excited into population inversion and thereby participate in stimulated photon emission, leading to laser oscillation. YAG, because of its structural, thermal and crystalline characteristics, is a very useful host material which can be fabricated to yield rods of high optical quality. Rare Earth-doped YAG, containing for example holmium or erbium, produces principle laser emission at wavelengths in the mid-infrared, while the characteristic emission of Er:YAG at 2.94 μm is preferred. Erbium-related electronic pump transitions in laser medium 12, believed to be in the visible spectral region, are optically excited above the laser operating threshold by high-intensity light supplied by flashlamp 14. The flashlamp 14, which is commonly a broadband emission gas discharge tube such as a xenon flashlamp, provides optical energy at the appropriate erbium pump wavelengths in response to high-current electrical discharge from pump circuit 16.

Since the Er:YAG lower laser transition lifetime is considerably longer-lived than the upper laser transition lifetime (2 ms. compared to 0.1 ms.), the lower level is easily populated, rendering cw and q-switched operation problematic. Alternatively, pump energy is supplied to the laser rod 12 in the form of short optical pulses, on the order of hundreds of microseconds, during which the laser rod 12 is pumped well above laser operating threshold. In response, high-intensity laser light pulses are produced within the laser resonant cavity, a portion of which is coupled out through partially transmitting output mirror 18. Since the refractive index of the YAG crystal is temperature dependent, thermal gradients may cause distortion of the optical path within the laser cavity; this so-called "thermal lensing", if large enough, can render the laser cavity unstable for sustaining laser oscillation.

The conversion of energy from an electrical current pulse driving flashlamp 14 to a laser light output pulse is generally quite inefficient, and results in substantial heating of the laser material. Typical conversion efficiencies are on the order of a few percent or less. Er:YAG laser operation is particularly inefficient due to the relatively large difference between pump and laser electronic energy levels. The remainder of the pump energy is rapidly converted to heat and must be carried away by fluidic coolant 22, often demineralized water circulating through the pump cavity 20. Since pump energy is deposited in a reasonably short time, it is expected that little of it dissipates via coolant 22 during this time, leading to increased temperatures and temperature gradients within the laser rod 12. Laser gain, that is the specific conversion of pump light to laser emission, is adversely affected by temperature, and thermal lensing as well as gain profile are similarly influenced by transient thermal gradients. In repetitively pumped operation, there is additionally the cumulative heating effects resulting from non-uniform pump processes, such as light distribution within the laser rod 12 and thermal gradients from heat flow into the coolant 22. In general, laser systems behave in a complicated non-linear fashion, such that a change in one operating condition may affect other conditions as well as the laser output.

An important consideration for pumping efficiency and pulse repetition rate of Er:YAG lasers is the condition and manner in which optical pump energy is generated by flashlamp 14 and applied to laser rod 12. Referring to FIG. 2, the flashlamp pump circuit 16 applies high-current electrical pulses to the flash lamp 14 by the repetitive discharge of pulse-forming network 34. The high voltage power supply 32 energizes pulse-forming network 34, the degree to which determines the pulse energy and is adjusted by controller 30. The pulse repetition rate $f_{rr}$ is adjusted by the pulse trigger rate, again supplied by controller 30. High-current pump pulses are generated by pulse forming network 34, shown schematically in FIG. 3, which in essence comprises an LC network in series with the non-linear impedance presented by flashlamp 14. In operation, the storage capacitor 40 is charged by high voltage supply 32 to a predetermined value, whereupon at a predetermined rate $f_{rr}$, trigger signal 46 closes SCR 44, allowing capacitor 40 to discharge through inductor 42 and flashlamp 14,- thereby producing a high-current pulse through flashlamp 14.

Figure 4:
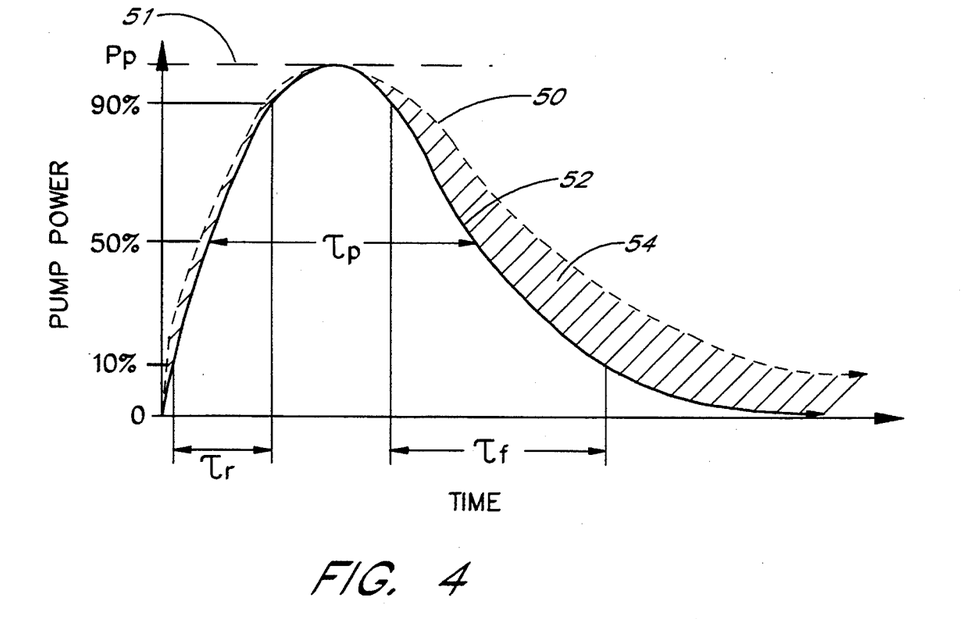
FIG. 4 is a sketch representing the optical pump power as a function of time.

The flashlamp 14 output power as a function of time for a representative pump pulse is shown in FIG. 4, curve 50. An important pulse characteristic influencing laser operation is the pump pulse energy $E_p$, represented here by the total integrated area under the pulse power curve 50. In operation, for a given flashlamp 14 and pulse-forming network 34, achieving a specific pump pulse energy will require a corresponding pulse duration $\tau_p$, defined herein as the time during which the instantaneous pump power is greater than or equal to 50% of the peak instantaneous power $P_p$. Similarly, pulse rise and fall time $\tau_{r,f}$ are defined herein as the time during which the instantaneous pump power is between 10% and 90% of the peak instantaneous power for the leading and trailing edge of the pulse, respectively. Pump pulses commonly used for surgical applications may have pulse durations of hundreds of microseconds, but typically also with significantly long pulse rise and fall times. In the preferred embodiment, the flashlamp 14 is energized with pulses of the desired magnitude, duration, shape and repetition rate to affect tissue cutting while minimizing laser instability. Accordingly, it is found that effective laser operation at high pulse repetition rate is obtained when pump pulse energy is reduced and delivered to the laser medium 12 in a short time duration. Thus, the characteristic pump pulse times $\tau_{p,r,f}$ are short or equivalently, the ratio of pump energy to peak power is small. To achieve this condition, in general there is a balance between the capacitance C of storage capacitor 40 and inductance L of inductor 42 in the presence of flashlamp 14 non-linear impedance: for C too high the discharge is heavily damped and for L too high the discharge oscillates. In both cases the pump pulse duration and fall-time is long, as indicated by the tail of curve 50. In the preferred embodiment, the values of C and L are tuned to provide a high-current discharge across flashlamp 14, sufficient to produce the desired tissue modification, while, in addition, characterized by a short pulse duration and short pulse rise- and fall-time. Thus, for a given peak power, the optimized condition corresponds to a substantially critically damped discharge, where now the pulse duration and pulse rise and fall times are minimized.

The preferred flashlamp power output resulting from the above condition is depicted in FIG. 4, curve 52, which represents the fastest, most-efficient transfer of electrical to optical pump energy. This condition presents several distinct advantages for laser operation in general and surgical applications in particular. From the perspective of high-power, pulsed operation, the overall conversion efficiency is improved due to the impedance match between pulse forming network 34 and flashlamp 14. For the case of relatively inefficient Er:YAG, a short rise-time is preferred in order to achieve laser output well-above threshold, while the short fall-time is preferred to allow the long-lived lower laser transition to depopulate before the next pump pulse. Furthermore, the preferred pump pulse minimizes the pump time duration for a given pulse energy or as illustrated in FIG. 4 minimizes the ratio of pulse energy to peak power. The hatched area 54 represents energy saved by utilizing the optimized pump pulse, energy which would otherwise contribute to thermal instability.

Simmer supply 36 comprising a DC current source, is used to excite flashlamp 14 in a continuous manner at a power level sufficient to maintain laser rod 12 substantially at, but below, laser threshold, indicated in FIG. 5 by $P_t$ (53). This embodiment presents several advantages contributing to increased pulse repetitions rate. By maintaining laser rod 12 nominally at laser threshold, the response of pulse-forming network 34 is considerably improved, meaning shortened pulse durations as well as rise/fall times. Moreover, thermal equilibrium is established in laser rod 12 via contact with coolant 22 under operating conditions where pulsed power input is more efficiently coupled into laser light output, thus reducing transient heating and attenuating the demand on pulse-forming network 34. Furthermore, a continuous discharge maintained in flashlamp 14 lowers the effective impedance and non-linearities thereof presented to pulse-forming network 34, thereby contributing to a shorter pulsed discharge.

Figure 5:
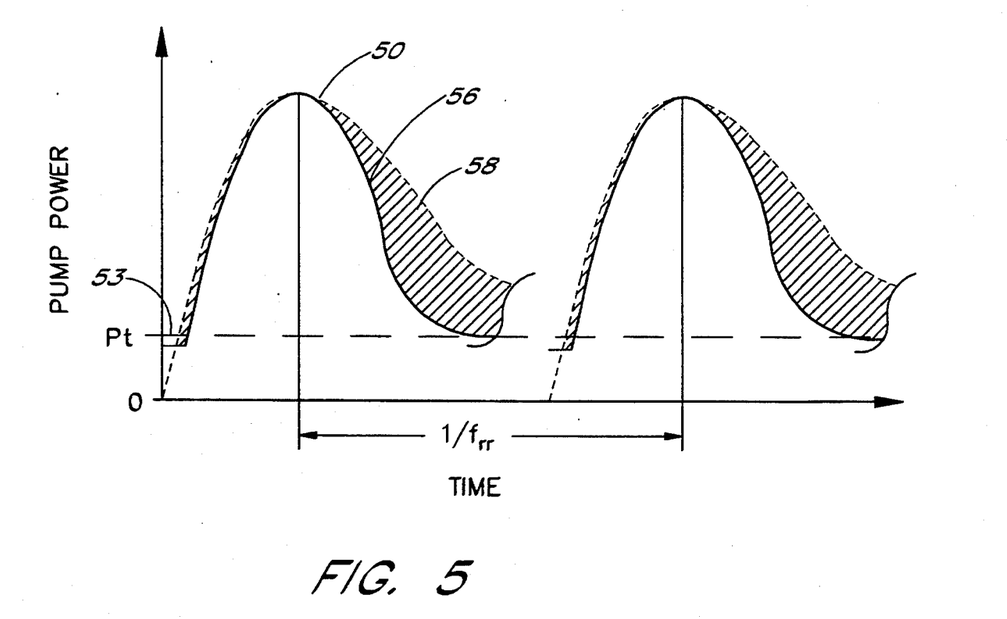
FIG. 5 is a sketch representing the optical pump power including simmer supply contribution as a function of time.

Curve 50 of FIG. 5 represents a common pump pulse sequence where laser rod 12 is brought from quiescent to high-power within a pulse period, followed by a long relaxation where energy is dissipated by laser rod 12. The sequence is repeated for every laser pulse at a repetition rate $f_{rr}$. Curve 56 represents the modified pump power using an efficient pulse-forming network 34 in combination with simmer supply 36 which maintains a continuous pump power near the level $P_t$, corresponding to laser operating threshold. The energy saved is represented by the hatched area 58, which would otherwise contribute to thermal instability and laser output deleterious for tissue modification. Since the transient pump energy necessary to achieve a given output energy is reduced, transient heating is likewise reduced. As seen in FIG. 5, it is apparent that the preferred pump circuit, comprising of simmer supply 36 in conjunction with pulse forming network 34, functions to distribute the pump power to laser rod 12 more uniformly over time, thereby reducing thermal instability due to transient heating. The energy demands per pulse are reduced, as is the impedance of flashlamp 14, allowing adjustment of capacitor 40 and inductor 42 in pulse-forming network 34 to further reduce the rise/fall-time of the current discharge through flashlamp 14. Thus, there is an important element of synergism between the simmer supply 36, pulse-forming network 34, reduced thermal instability and increased pulse repetition rate.

A reflective ellipsoidal pump cavity preferably encloses flashlamp 14 and laser rod 12. An optically diffusive pump cavity 60, shown in FIG. 6a is commonly used in optical pumping arrangements based on their simplicity and potential robust construction. The rough surfaces of pump cavity 60 scatter light emitted by flashlamp 14, presumably uniformly throughout cavity 60, represented by rays 64 in FIG. 6a. The laser rod 12, however, is not necessarily uniformly excited or heated over the rod cross-section, and in particular may develop hot spots influencing the gain profile and thermal lensing. In contrast, optical pump cavity 62 of FIG. 6b represents a reflective elliptical cylinder, wherein flashlamp 14 and laser rod 12 are located along each of the ellipse foci. From geometrical considerations, light rays emerging radially outward from flashlamp 14 are reflected by the ellipse wall onto the axis of laser rod 12, as depicted by rays 66. Such radially isotropic excitation improves the cumulative gain profile and attenuates thermal gradients within laser rod 12, thereby minimizing thermal lensing. The highly reflective surfaces of elliptical pump cavity 62 also absorb less radiation than a diffusive surface, and thus acts synergistically with other improvements to increase the overall conversion efficiency, thereby minimizing the pulse energy necessary to obtain a given operating condition. Thermal lensing, gain profile and pump energy are all affected advantageously by pump cavity 62, and consequently the pulse repetition rate may be increased.

Figure 7A:
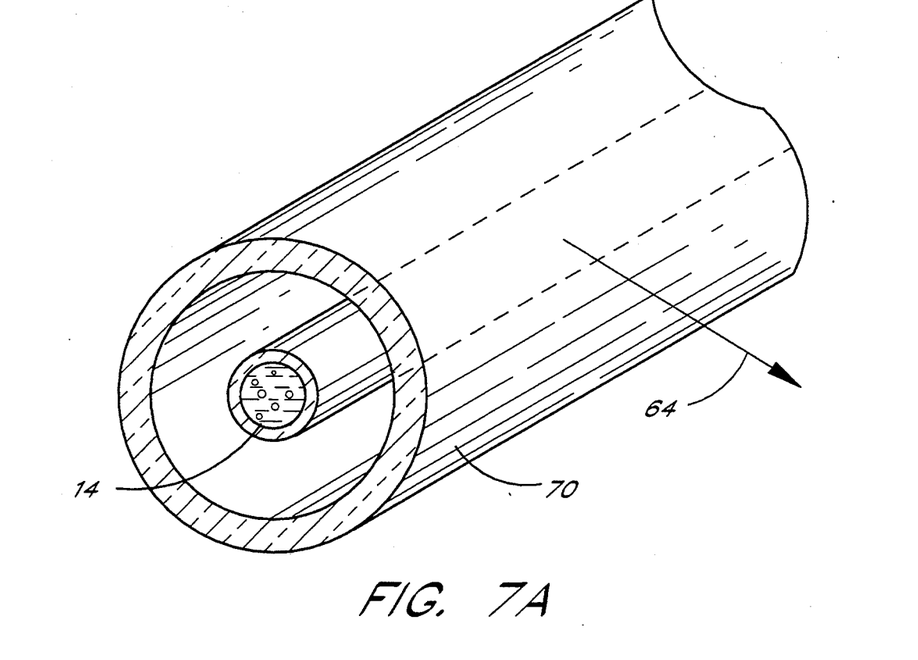
FIG. 7a is a cross-sectional perspective of the optical pump spectral filter in region 7 of FIG. 6, and 7b is a sketch representing the spectral radiance and transmittance of flashlamp and filter, respectively.
Figure 7B:
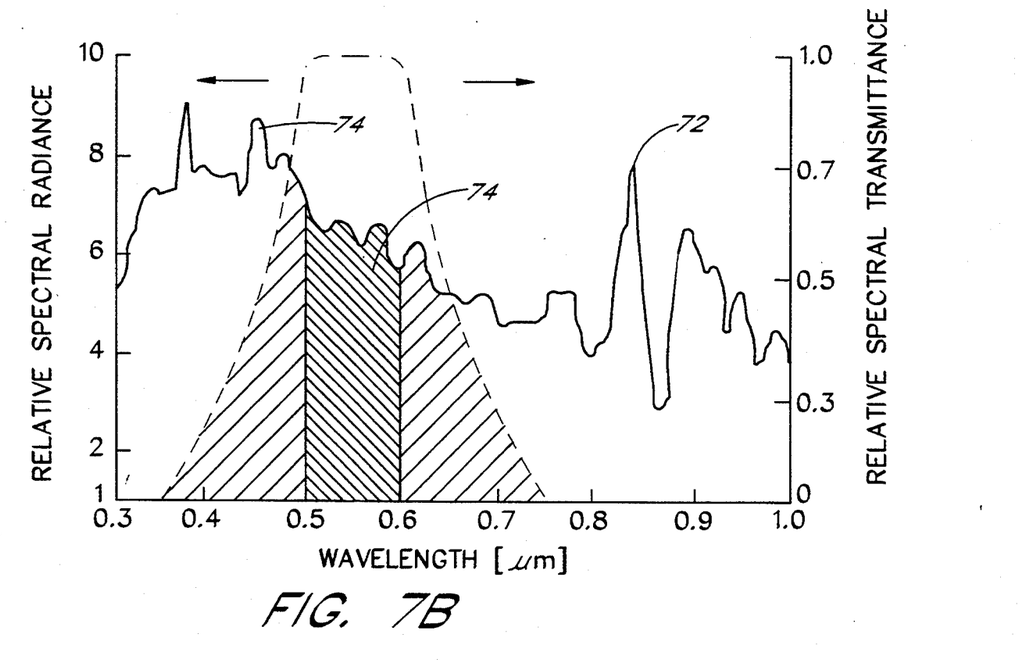

A spectral filter 70, shown in a close-up cross-sectional perspective in FIG. 7a, comprises a cylindrical sheath of uranium-doped glass, placed concentrically around flashlamp 14, laser rod 12 or both, thereby filtering flashlamp light emission 64 before irradiating laser rod 12. The spectral filter 70, is shown in FIG. 7a positioned concentrically around flashlamp 14, however it should be understood that the preferred embodiment may also comprise placement around laser rod 12 as well. Typical flashlamps, such as a xenon-filled quartz tube, will emit radiation over a broad spectral range, which is advantageous for utilizing a plurality of pump transitions in laser medium 12, but which nevertheless contribute to heating by also exciting transitions not useful for laser oscillation. A band of useful pump transitions 74 is shown in FIG. 7b, superposed on a typical flashlamp spectral radiance curve 72, which serves to highlight the excess energy supplied to laser rod 12. This excess energy increases thermal instability and limits the pulse repetition rate. Spectral filter 70 is configured to selectively absorb optical power from flashlamp 14 which lies outside the laser pump transition band 74, represented in FIG. 7b by spectral transmittance curve 76. It is apparent that the ratio of useful power to absorbed power in laser rod 12 is increased by spectral filter 70. The thermal load on laser rod 12 for a given laser output power is thereby reduced and consequently allows higher pulse repetition rate. A further structural advantage provided by the cylindrical cavity of spectral filter 70 is exploited when fluidic coolant is directed through the volume between flashlamp 14 and spectral filter 70. The cylindrical channel functions to direct coolant along the length of the heat-bearing surfaces, thereby increasing the heat-exchange between coolant and surface.

Under normal operation, laser rod 12 is aligned within the optical resonant cavity defined by mirrors 18 such that laser oscillation is maintained for radiation that is substantially collimated within the resonator. Under these circumstances, flat mirror faces 80, indicated in FIG. 8, may be used to couple radiation back into the laser rod 12 or out of the laser cavity as laser output. With the demanding conditions of high peak powers, thermal lensing of the laser rod 12 may cause light rays traversing laser rod 12 to diverge, creating a so-called unstable resonant cavity. Such conditions are accompanied by degraded output mode quality and decrease of power. Schematically shown by rays 82, divergent rays are reflected out of the laser cavity region by mirror flats 80 and so cannot contribute to laser gain. In the preferred embodiment, curved mirrored surfaces 84 are incorporated to restore stable operation by reflecting divergent beams back onto the resonator axis, thereby maintaining laser oscillation. Thus, a slightly divergent beam can render useful laser output by corrective cavity mirrors 84. The improved laser cavity functions to maintain a stable high quality laser output in spite of some thermal lensing in laser rod 12. The ensuing expanded range of cavity stability provides an increase of laser output power for a given pump power level, or alternatively higher repetition rate beyond that possible with plane mirror surfaces 80. This embodiment likewise reduces power demands on pump circuitry 16, allowing shorter pump pulses to be used.

A considerable fraction of pump power is converted to heat as a result of conditions such as: quantum efficiency less than unity, energy difference between pump and laser transitions, and spectral range of pump light, all of which must be dissipated by fluidic coolant 22. Still another element of the preferred embodiment is an improved fluidic cooling system, whereby coolant 22 is directed substantially parallel to the surfaces of laser rod 12, flashlamp 14 and optical pump cavity 20, shown schematically in FIG. 9, and maintained in substantially laminar flow parallel to all heat-dissipating surfaces. Laminar flow of coolant 22 through laser head 26 is produced with a flow path of coolant 22 through laser head 26 characterized by relatively small angular displacements, directing flow substantially parallel to the internal surfaces and limiting flow velocity along internal surfaces. The flow path may be directed with spectral filters 70 positioned concentrically around both flashlamp 14 and laser rod 12 such that fluid flows through the cylindrical volume between the heat-bearing surfaces of spectral filter 70 and flashlamp 14 (or laser rod 12). Strictly laminar flow characteristics provide efficient, uniform coolant exchange via ducts 24, but allow, however, only conductive heat exchange between heat-dissipating surfaces—laser rod 12, flashlamp 14, spectral filter 70 and pump cavity 20—and fluidic coolant 22 at the surface/fluid interface. Therefore, in the preferred embodiment, a substantially laminar flow is maintained parallel to the heat-dissipating surfaces, while a small degree of non-laminar or turbulent flow persists in the immediate vicinity of the surface/fluid interface, thereby providing a greater degree of heat transfer. Such conditions are generated by increasing the flow velocity to a degree above which turbulent flow is generated at the surface/fluid interface. The preferred flow conditions are depicted in FIG. 9 where substantially laminar flow is maintained in regions 90, while some degree of non-laminar flow persists in regions 92. Non-laminar flow near the hot surfaces increases convective heat exchange at the boundary surfaces, while not detracting significantly from coolant flow through laser head 26. A more efficient fluidic cooling system functions to reduce long-term or cumulative heating effects in laser rod 12, thus allowing higher pulse repetition rate. Furthermore, a synergistic improvement is created because the efficient fluidic cooling system complements the pump pulse sequence utilizing a continuous power source.

A surgical method preferably utlizing the embodiments disclosed herein comprises directing light pulses at tissue to be modified, wherein the light pulses have a wavelength between 1.7 μm and 4.0 μm with pulse energy less than 1 Joule and a pulse repetition rate greater than 10 pulses per second (PPS). The pulsed energy may preferably have a pulse duration less than 500 μs. Effective tissue modification accompanied by reduced tissue damage is achieved with a radiant exposure preferably less than 2.0 J/mm²/pulse and in some embodiments such exposure is less than about 1.5 J/mm²/pulse. Table I lists a number of preferred laser surgical applications utilizing low pulse energy and high pulse repetition rate, and indicates preferred values or ranges for pulse energy, repetition rate and spot size.

TABLE I

| Application | Preferred Values | | |
|---|---|---|---|
| | Pulse Energy (J) | Repetition Rate (PPS) | Spot Diameter (mm) |
| Dental (Er:YAG preferred) | | | |
| Hard Tissue Etching | .025 | 10–20 | .25–.32 |
| Enamel Cutting | .150 | 10–20 | .25–.32 |
| Dentin Removal | .08–.12 | 10–20 | .25–.32 |
| Surgery | .05–.08 | 30–50 | .25–.32 |
| Soft Tissue Incision | | | |
| Ophthalmology | | | |
| Sclerostomy | .01 | 10–20 | .40 |
| Laser Lens Emulsification | .03–.05 | 10–30 | .60–.80 |
| Corneal Sculpting | .70–1.0 | 10–30 | 6.0–8.0 |
| Orthopedics & | .08–.25 | 10–30 | .25–.32 |

TABLE I-continued

| Application | Preferred Values | | |
|---|---|---|---|
| | Pulse Energy (J) | Repetition Rate (PPS) | Spot Diameter (mm) |
| Periodontics (Ho:YAG preferred) | | | |
| Bone | | | |

Except for the corneal sculpting application (in which the light is transmitted by free space delivery), the above applications preferably employ an optical waveguide such as in optical fiber to direct the optical energy at the tissue. In the mid-infrared spectral region and under conditions of high intensity light transmission, many optical fibers become absorptive or lossy. The absorbed radiation contributes significantly to fiber degradation and increases demands on laser output. The prefered embodiments disclosed herein help to circumvent this problem because for a given average power level, light pulses of lower energy and higher repetition rate undergo less attenuation in optical fiber transmission.

The present invention has been described herein with specific reference to the preferred embodiments thereof. However, those skilled in the art will understand that changes may be made in the form of the invention covered by the claims without departing from the scope and spirit thereof, and that certain features of the invention may sometimes be used to advantage without corresponding use of other features.

We claim:

1. A pulsed, optically pumped laser, comprising:
   a source of pump light;
   a resonant cavity comprising a laser material positioned for pumping by said pump light, said laser material emitting light having a wavelength between 1.7 μm and 4 μm in response to pumping by said pump light; and
   a circuit for energizing said source of pump light to produce pulsed optical pump energy at a pulse repetition rate of more than 10 pulses per second, whereby said resonant cavity produces laser pulses at said repetition rate, the intensity of the pump pulses having rise and fall times sufficiently short to partially avoid thermal lensing induced instability of said laser pulses in said resonant cavity at said pulse repetition rate.

2. The pulsed, optically pumped laser of claim 1, wherein the pulse repetition rate is at least 20 pulses per second.

3. The pulsed, optically pumped laser of claim 1, wherein the energy of said laser pulse is less than 1 J.

4. The pulsed, optically pumped laser of claim 1, wherein the pulse duration of said laser pulse is less than 500 μs.

5. The pulsed, optically pumped laser of claim 4, wherein said source of pump light and said laser medium are positioned within a reflective cylindrical cavity of elliptical cross section such that the axis of each of said source of pump light and said laser medium are substantially colinear with different foci of the ellipse.

6. The pulsed, optically pumped laser of claim 1, wherein said circuit energizes said source of pump light during the interpulse period to supply pump energy to said laser medium at a level sufficient to maintain said laser medium substantially at, but below, the laser threshold of said lasing medium.

7. The pulsed, optically pumped laser of claim 6, wherein is an optical filter, positioned to intercept substantially all of the radiation emitted by said source of pump light and having a maximum relative spectral transmittance at optical wavelengths which correspond to the pump wavelengths of said laser medium.

8. The pulsed, optically pumped laser of claim 1, wherein said resonant cavity includes a reflector configured to at least partially compensate thermal lensing effects in said laser medium.

9. The pulsed, optically pumped laser of claim 1, wherein flows a fluidic coolant for cooling said laser medium, said fluidic coolant having a flow path configured to maintain substantially laminar flow in a direction parallel to a surface of said laser medium except at the boundary between the fluid and said surface of said laser medium.

10. The pulsed laser of claim 9, wherein the laser light output is comprised of pulses having a pulse energy less than 1 J.

11. The pulsed laser of claim 9, wherein the pulse repetition rate is greater than 10 pulses per second.

12. The pulsed laser of claim 11, wherein is an optical filter positioned to intercept substantially all of the pump light emitted by said source of pump light and which preferentially absorbs pump light at wavelengths other than the pump wavelengths of said laser medium.

13. The pulsed laser of claim 9, wherein is an optical pump cavity comprised of reflective ellipsoidal cylinder within which is positioned said source of pump light and said laser medium such that each is aligned with a different focal line of the ellipsoid.

14. A pulsed laser, comprising:

a source of pump light;

an optical resonator cavity comprising a laser medium and reflectors, said laser medium emitting light between 1.7 $\mu$m and 4 $\mu$m in response to pumping with said pump light, one of said reflectors being partially transmitting to produce laser light output and at least one of said reflectors comprising a curved mirror, the curvature of said mirror being selected to at least partially compensate thermal lensing effects in said lasing medium;

a fluidic system for cooling said lasing medium, said system being configured to provide a substantially laminar flow through a portion of said optical resonator cavity containing said lasing medium in a direction parallel to a surface of said laser medium except at the boundary between the fluid and said surface of said lasing medium; and an electrical circuit which produces electrical pulses for energizing said pump source, said electrical pulses having a ratio of total energy to peak power less than 500 $\mu$s, said electrical circuit supplying interpulse energy to said pump source between said pulses, said interpulse energy energizing said pump source to supply sufficient pump energy to said lasing medium to hold said lasing medium substantially at, but below, the laser threshold of said laser medium.

* * * * *